United States Patent
Rich

(10) Patent No.: US 8,017,402 B2
(45) Date of Patent: Sep. 13, 2011

(54) FLUIDIC SYSTEM FOR A FLOW CYTOMETER

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 157 days.

(21) Appl. No.: 11/370,714

(22) Filed: Mar. 8, 2006

(65) Prior Publication Data

US 2007/0212262 A1 Sep. 13, 2007

(51) Int. Cl.
*G01N 35/08* (2006.01)
*G01N 33/48* (2006.01)

(52) U.S. Cl. ......... 436/63; 436/164; 436/177; 422/73; 422/82.05; 422/400; 356/39; 356/72; 356/246; 356/335

(58) Field of Classification Search ............. 422/73, 422/82.05, 100; 436/63, 52, 164; 356/244, 356/246, 440
See application file for complete search history.

(56) References Cited

U.S. PATENT DOCUMENTS

| | | |
|---|---|---|
| 3,347,273 A | 10/1967 | Russell |
| 3,601,128 A | 8/1971 | Hakim |
| 3,672,402 A | 6/1972 | Bloemer |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,790,653 A | 12/1988 | North, Jr. |
| 4,818,103 A | 4/1989 | Thomas et al. |
| 4,844,610 A * | 7/1989 | North, Jr. .................. 356/73 |
| 5,040,890 A * | 8/1991 | North, Jr. .................. 356/72 |
| 5,043,706 A | 8/1991 | Oliver |
| 5,083,862 A | 1/1992 | Rusnak |
| 5,155,543 A | 10/1992 | Hirako |
| 5,395,588 A | 3/1995 | North, Jr. |
| 5,403,552 A | 4/1995 | Pardikes |
| 5,539,386 A | 7/1996 | Elliott |
| 5,552,885 A | 9/1996 | Steen |
| 5,797,430 A | 8/1998 | Becke et al. |
| 6,039,078 A | 3/2000 | Tamari |
| 6,070,477 A | 6/2000 | Mark |
| 6,110,427 A * | 8/2000 | Uffenheimer ............... 422/81 |
| 6,156,208 A | 12/2000 | Desjardins et al. |
| 6,183,697 B1 | 2/2001 | Tanaka |
| 6,288,783 B1 | 9/2001 | Auad |
| 6,382,228 B1 | 5/2002 | Cabuz |
| 6,427,521 B2 | 8/2002 | Jakkula et al. |
| 6,431,950 B1 | 8/2002 | Mayes |

(Continued)

FOREIGN PATENT DOCUMENTS

EP 1521076 4/2005

(Continued)

*Primary Examiner* — P. Kathryn Wright
(74) *Attorney, Agent, or Firm* — Jeffrey Schox

(57) ABSTRACT

The fluidic system of the preferred embodiment includes a sheath pump to pump sheath fluid from a sheath container into an interrogation zone and a waste pump to pump waste fluid from the interrogation zone into a waste container. The sheath pump and/or the waste pump draw sample fluid from a sample container into the interrogation zone. The fluidic system also includes a controller to adjust the flow rate of the sample fluid from the sample container into the interrogation zone. The fluidic system is preferably incorporated into a flow cytometer with a flow cell that includes the interrogation zone.

15 Claims, 2 Drawing Sheets

U.S. PATENT DOCUMENTS

| | | |
|---|---|---|
| 6,456,769 B1 | 9/2002 | Furusawa et al. |
| 6,568,271 B2 | 5/2003 | Shah et al. |
| 6,602,469 B1 | 8/2003 | Maus et al. |
| 6,694,799 B2 | 2/2004 | Small |
| 6,718,415 B1 | 4/2004 | Chu |
| 6,825,926 B2 * | 11/2004 | Turner et al. ............ 356/244 |
| 6,852,284 B1 * | 2/2005 | Holl et al. ................. 422/68.1 |
| 6,872,180 B2 | 3/2005 | Reinhardt et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,941,005 B2 | 9/2005 | Lary et al. |
| 7,019,834 B2 | 3/2006 | Sebok et al. |
| 7,061,595 B2 | 6/2006 | Cabuz |
| 7,105,355 B2 | 9/2006 | Kurabayashi et al. |
| 7,328,722 B2 | 2/2008 | Rich |
| 7,403,125 B2 | 7/2008 | Rich |
| 7,520,300 B2 | 4/2009 | Rich |
| 7,628,956 B2 | 12/2009 | Jindo |
| 2002/0028434 A1 | 3/2002 | Goix |
| 2002/0059959 A1 | 5/2002 | Qatu et al. |
| 2002/0123154 A1 | 9/2002 | Burshteyn |
| 2003/0054558 A1 | 3/2003 | Kurabayashi |
| 2003/0062314 A1 | 4/2003 | Davidson et al. |
| 2003/0072549 A1 | 4/2003 | Facer et al. |
| 2003/0129090 A1 | 7/2003 | Farrell |
| 2003/0175157 A1 | 9/2003 | Micklash, II et al. |
| 2003/0202175 A1 | 10/2003 | Van den Engh et al. |
| 2003/0211009 A1 | 11/2003 | Buchanan |
| 2003/0223061 A1 | 12/2003 | Sebok |
| 2004/0031521 A1 | 2/2004 | Vrane et al. |
| 2004/0112808 A1 | 6/2004 | Takagi et al. |
| 2004/0123645 A1 | 7/2004 | Storm, Jr. et al. |
| 2005/0069454 A1 | 3/2005 | Bell |
| 2005/0195684 A1 | 9/2005 | Mayer |
| 2005/0252574 A1 | 11/2005 | Khan et al. |
| 2006/0177937 A1 | 8/2006 | Kurabayashi et al. |
| 2006/0286549 A1 | 12/2006 | Sohn |
| 2007/0003434 A1 | 1/2007 | Padmanabhan |
| 2007/0212262 A1 | 9/2007 | Rich |
| 2007/0224684 A1 | 9/2007 | Olson et al. |
| 2009/0104075 A1 | 4/2009 | Rich |

FOREIGN PATENT DOCUMENTS

| | | |
|---|---|---|
| WO | 2005017499 | 2/2005 |
| WO | WO/2005/017499 | 2/2005 |

* cited by examiner

FLUIDIC SYSTEM FOR A FLOW CYTOMETER

TECHNICAL FIELD

This invention relates generally to the flow cytometer field, and more specifically to an improved fluidic system in the flow cytometer field.

BACKGROUND

The fluidic system of a conventional flow cytometer incorporates an air and/or vacuum pump to pressurize and pump sheath fluid from a high-pressure container to the interrogation zone of a flow cell. These fluidic systems are typically arduous to assemble (which increases the costs of the flow cytometer), heavy to haul (which limits the repair options), and challenging to calibrate (which induces errors in the data). Thus, there is a need in the flow cytometer field to create an improved fluidic system. This invention provides such improved fluidic system for a flow cytometer.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

Figure 1:
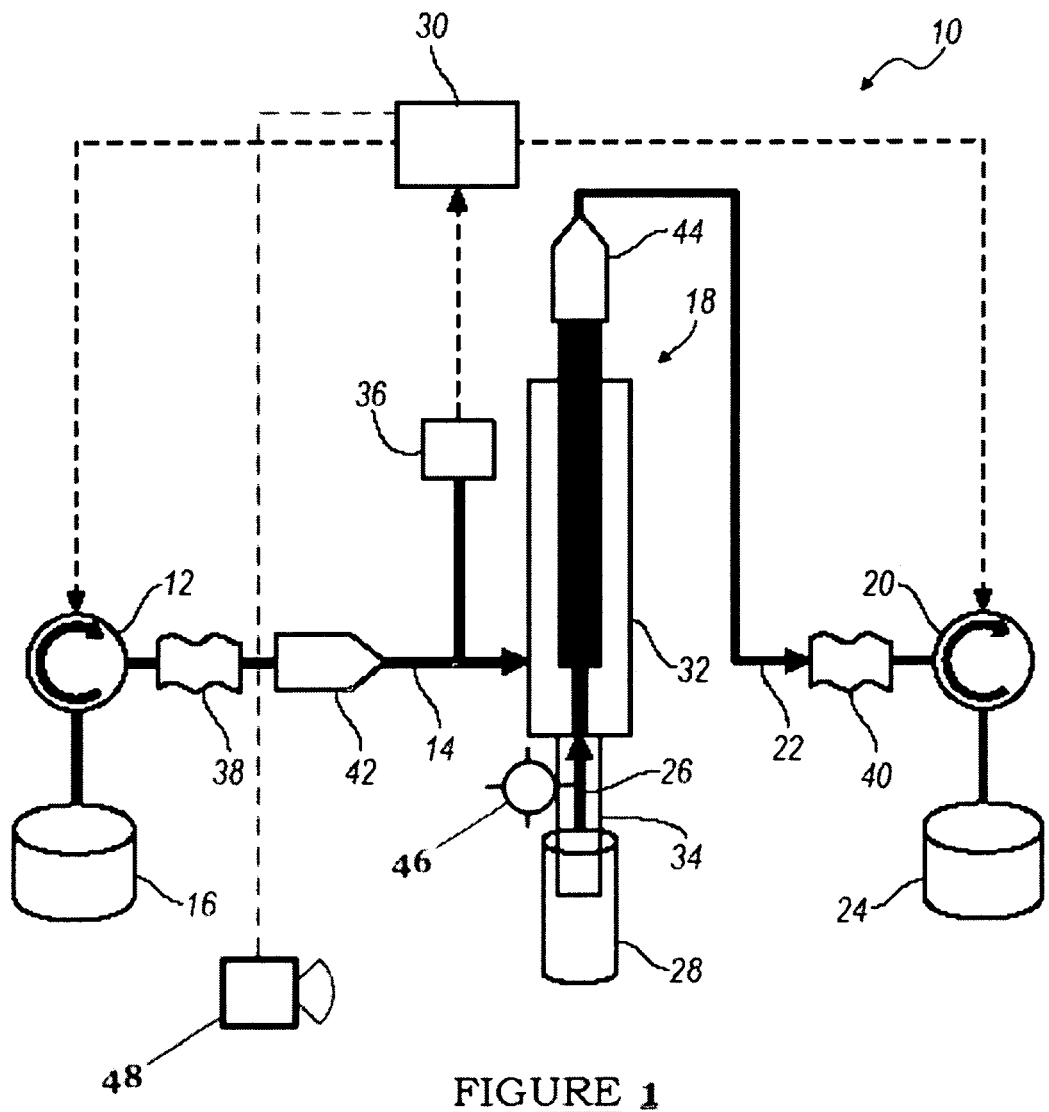
FIG. 1 is a schematic representation of the fluidic system of the preferred embodiment of the invention.
Figure 2:
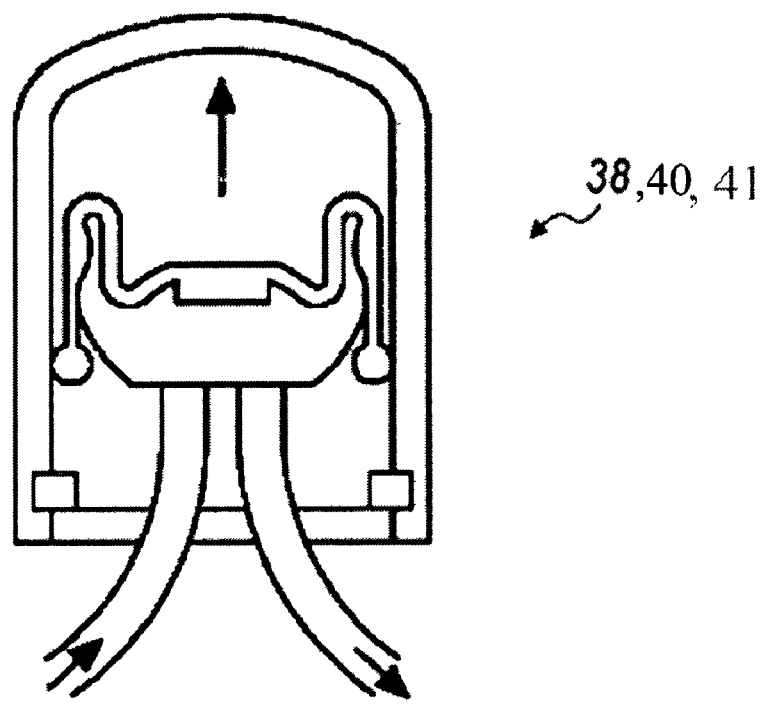
FIGS. 2 and 3 are variations of the fluidic capacitors.
Figure 3:
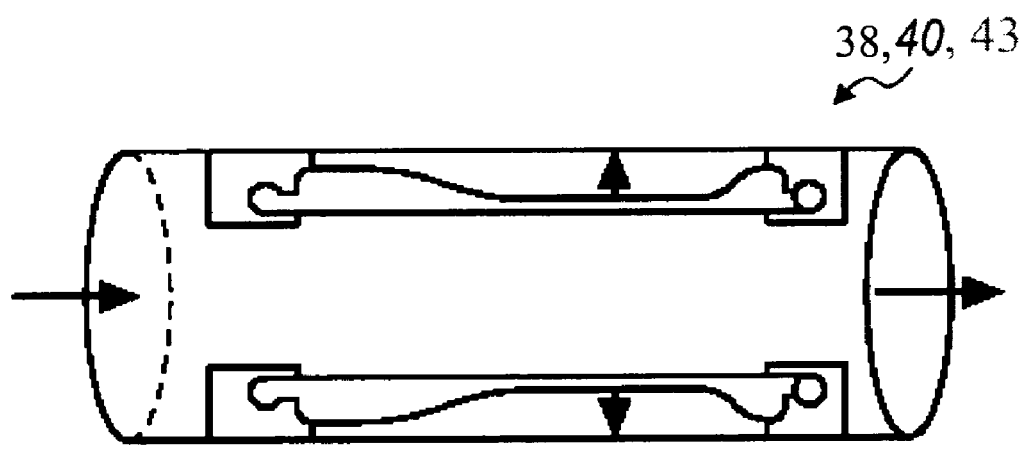

As shown in FIG. 1, the fluidic system 10 to of the preferred embodiment includes a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a controller 30 to adjust the flow rate of the sample fluid 26 from the sample container 28 into the interrogation zone 18. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 32, but may alternatively be defined by any suitable system or device. The fluidic system 10 is preferably incorporated into a flow cytometer, but may be alternatively incorporated into any suitable system that pumps a first fluid from a first container into an interrogation zone, draws a second fluid from a second container into the interrogation zone, and pumps the combined fluids from the interrogation zone into a third container.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 32 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system lo is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from a waste container 24 into an interrogation zone 18.

The sheath pump 12 and the waste pump 20 of the preferred embodiment cooperate to draw the sample fluid 26 from the sample container 28 and through a drawtube 34. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 34, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. In a fourth variation, the sheath pump 12 and the waste pump 20 are driven by separate motors with separate controls and, therefore, allows for a variable flow rate of the sheath fluid 14 and/or waste fluid 22. The fluidic system 10 may, however, include other suitable variations that draw the sample fluid 26 from the sample container 28 into the interrogation zone 18 through the use of a pressure differential.

The controller 30 of the preferred embodiment functions to adjust the flow rate of the sample fluid 26 from the sample container 28 into the interrogation zone 18. Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input. The controller 30 is preferably a proportional-integral-derivative (PID) controller, but may alternatively be a proportional-integral (PI) controller, a proportional-derivative (PD) controller, a proportional (P) controller, or any other suitable controller.

The fluidic system 10 of the preferred embodiment also includes a pressure sensor 36 that functions to measure a pressure of the sheath fluid 14 as close as possible to the inlet for the sample fluid 26. This measured pressure is an adequate estimate for the pressure of the sample fluid 26. The pressure sensor 36 preferably measures a pressure differential between the top of the drawtube 34 near the flow cell 32 and the bottom of the drawtube 34 near the sample container 28, but may alternatively measure a pressure differential between the drawtube 34 and atmosphere. The controller 30 is preferably connected to the pressure sensor 36 and adjusts the flow rate of the sample fluid 26 based on the measured pressure. The controller 30 may alternatively or additionally be connected to other suitable devices to assist in the control of the flow rate of the sample fluid 26. In a first variation, the fluidic system 10 may include a flow meter 46 that functions to measure the flow rate of the sample fluid 26 from the sample container 28 into the interrogation zone 18. In a second variation, the fluidic system 10 may include an input device 48 that functions to receive information related to a fluidic resistance of a drawtube 34 that transports the sample fluid 26 from the sample container 28 into the interrogation zone 18. The input device 48 is preferably an optical device (e.g., a bar code scanner) or an electromagnetic device (e.g., a RFID receiver) that functions to automatically scan and read a code on the drawtube 34. The code is preferably cross-referenced with empirically derived information regarding the fluidic resistance of the drawtube 34. The input device 48 may alternatively be a user-interface device that accepts a code or value related to the fluidic resistance of the drawtube 34. In a third variation, the fluidic system 10 may be substantially self-calibrating according to the following steps: the user places a drawtube 34 of the flow cell 32 into a known fluid (such as buffered saline), the user pumps waste fluid 22 from the interrogation zone 18 into a waste container 24 while maintaining a negligible flow rate of the sheath fluid 14 thereby drawing the known fluid through the drawtube 34 and into the interrogation zone 18, and the fluidic system 10 (through measurement of the flow rate of the waste fluid 22 or any other suitable parameter) estimates the resistance of the drawtube 34. With this estimated resistance of the drawtube 34 for the flow cell 32 combined with the measured pressure of the sheath fluid 14, the controller 30 adjusts the flow rate of the sample fluid 26 with greater accuracy and control.

The fluidic system 10 of the preferred embodiment also includes a first fluidic capacitor 38 located between the sheath container 16 and the interrogation zone 18 and a second fluidic capacitor 40 located between the interrogation zone 18 and the waste container 24. The fluidic capacitors 38 and 40 function to attenuate pulsations within the fluidic system 10. More specifically, the first fluidic capacitor 38 functions to temporarily expand/contract to thereby accumulate/release the sheath fluid 14 and attenuate pulsations within the sheath fluid 14. Similarly, the second fluidic capacitor 40 functions to temporarily expand/contract to thereby accumulate/release the waste fluid 22 and attenuate pulsations within the waste fluid 22. The fluidic capacitors 38 and 40 are selected from the group consisting of bellows-type 41 with a diaphragm, bellows-type 41 without a diaphragm, captive ball-type, and flexible tube-type 43. The fluidic capacitors 38 and 40 are preferably similar to the fluidic attenuators described in U.S. patent application Ser. No. 11/297,667 entitled "Pulsation Attenuator For A Fluidic System" and filed 7 Dec. 2005, which is hereby incorporated in its entirety by this reference. The fluidic capacitors 38 and 40 may, however, be any suitable device to attenuate pulsations within the fluidic system 10.

The fluidic system 10 of the preferred embodiment also includes a valve 42 located between the first fluidic capacitor and the interrogation zone 18, and a valve 44 located between the interrogation zone 18 and the second fluidic capacitor. The valves 42 and 44 function to facilitate the control of the sheath fluid 14 and the waste fluid 22. The valves 42 and 44 are preferably check-valves, but may alternatively be any suitable valve to facilitate the control of the sheath fluid 14 and the waste fluid 22.

The fluidic system 10 of the preferred embodiment is preferably operated with the following steps: (1) pumping sheath fluid 14 from a sheath container 16 into an interrogation zone 18 and pumping the sheath fluid 14 and the sample fluid 26 as waste fluid 22 from the interrogation zone 18 into a waste container 24, thereby drawing sample fluid 26 from a sample container 28 into the interrogation zone 18; and (2) adjusting the flow rate of the sample fluid 26 from the sample container 28 into the interrogation zone 18. As explained above, step (2) preferably includes allowing a substantially adjustable flow rate of the sheath fluid 14 from the sheath container 16 to the interrogation zone 18, while maintaining a substantially consistent flow rate of the waste fluid 22 from the interrogation zone 18 into the waste container 24. The operation of the fluidic system lo also preferably includes attenuating pulsations within the sheath fluid 14 and the waste fluid 22.

As a person skilled in the art of flow cytometers will recognize from the previous detailed description and from the figures and claims, modifications and changes can be made to the preferred embodiment of the invention without departing from the scope of this invention defined in the following claims.

I claim:

1. A fluidic system for pumping sheath fluid from a sheath container and sample fluid from a sample container into an interrogation zone of a flow cytometer, comprising:
   a sheath pump that pumps sheath fluid from the sheath container into the interrogation zone of the flow cytometer;
   a waste pump that pumps waste fluid from the interrogation zone into a waste container;
   a drawtube, coupled to the sample container, that conveys the sample fluid from the sample container to the interrogation zone;
   a motor with motor controls coupled to at least one of the pumps of the fluidic system;
   a first fluidic capacitor located between the sheath pump and the interrogation zone and that temporarily expands and accumulates the sheath fluid to attenuate pulsations within the sheath fluid;
   a controller connected to the motor that adjusts the flow rate of the sample fluid from the sample container into the interrogation zone; and
   a pressure sensor that measures a pressure differential of the sample fluid between the top of the drawtube and the bottom of the drawtube,
   wherein the controller is coupled to the pressure sensor and adjusts the flow rate of the sample fluid based on the measured pressure differential, wherein the controller adjusts the flow rate of the sample fluid by adjusting the flow rate of the sheath fluid from the sheath container to the interrogation zone while simultaneously maintaining a substantially consistent flow rate of the waste fluid from the interrogation zone into the waste container.

2. The fluidic system of claim 1, wherein the controller is a proportional-integral-derivative controller (PID controller).

3. The fluidic system of claim 1, wherein the first fluidic capacitor is selected from the group consisting of bellows-type and flexible tube-type.

4. The fluidic system of claim 1, further comprising a check-valve located between the first fluidic capacitor and the interrogation zone.

5. The fluidic system of claim 1, further comprising a second fluidic capacitor located between the interrogation zone and the waste container that temporarily expands and accumulates the waste fluid to attenuate pulsations within the waste fluid.

6. The fluidic system of claim 5, wherein the second fluidic capacitor is selected from the group consisting of bellows-type and flexible tube-type.

7. The fluidic system of claim 5, further comprising a check-valve located between the interrogation zone and the second fluidic capacitor.

8. The system of claim 1, wherein the waste fluid is the combination of sample fluid and sheath fluid.

9. The system of claim 1, wherein the sheath pump and waste pump cooperate to create a fluidic pressure differential.

10. The system of claim 9, wherein the sheath pump pushes sheath fluid from the sheath container into the interrogation zone and the waste pump pulls the waste fluid from the interrogation zone into the waste container.

11. The system of claim 10, wherein the sheath pump and waste pump have a known flow rate to speed ratio and the controller controls the speed of at least one of the sheath pump and waste pump.

12. The fluidic system of claim 11, wherein the sheath pump is a peristaltic pump.

13. The fluidic system of claim 12, wherein the waste pump is a peristaltic pump.

14. A method for pumping sheath fluid from a sheath container and sample fluid from a sample container into an interrogation zone of a flow cytometer using the fluidic system of claim 1, comprising the steps of:
   a. simultaneously pumping sheath fluid from the sheath container into the interrogation zone of the flow cytometer and pumping waste fluid from the interrogation zone into the waste container, wherein the flow rate of the sheath fluid is different from the flow rate of the waste fluid thereby drawing sample fluid through the drawtube coupled to the sample container;
   b. measuring a pressure differential in the sample fluid pressure by the pressure sensor that measures the sample fluid between the top of the drawtube and the bottom of the drawtube; and
   c. adjusting the flow rate of the sample fluid from the sample container into the interrogation zone based on the measured differential pressure, wherein adjusting the flow rate of the sample fluid includes adjusting the flow rate of the sheath fluid from the sheath container to the interrogation zone while simultaneously maintaining a substantially consistent flow rate of the waste fluid from the interrogation zone into the waste container.

15. The method of claim 14, further comprising the steps of attenuating pulsations within the sheath fluid; and attenuating pulsations within the waste fluid.

* * * * *